United States Patent [19]
Masson

[11] Patent Number: 6,059,454
[45] Date of Patent: May 9, 2000

[54] AUTOCLAVABLE X-RAY CASSETTE HOLDER WITH HOLD-DOWN MEANS

[76] Inventor: Marcos V. Masson, 3221 Los Palmos, Houston, Tex. 77027

[21] Appl. No.: 09/039,109

[22] Filed: Mar. 13, 1998

[51] Int. Cl.[7] .................................................. G03B 42/02
[52] U.S. Cl. .......................................... 378/180; 378/177
[58] Field of Search ................................... 378/180, 177, 378/167, 182, 208

[56] References Cited

U.S. PATENT DOCUMENTS

| | | | |
|---|---|---|---|
| 5,243,639 | 9/1993 | Johnson | 378/180 |
| 5,327,912 | 7/1994 | Mally | 128/878 |

*Primary Examiner*—David P. Porta
*Attorney, Agent, or Firm*—Kenneth A. Roddy

[57] ABSTRACT

An autoclavable X-ray cassette holder removably receives and contains an X-ray cassette and maintains a patient's limb and/or extremities in a position on the holder relative to the X-ray cassette without requiring an attendant, thereby eliminating radiation exposure to the attendant. The holder has a thin rectangular hollow box-like main body formed of rigid radiolucent autoclavable material with an open end defining a central compartment surrounded by contiguous top and bottom walls, side walls, and an end wall. A plurality of slot-like depressions are formed along its side walls and end wall. An end cap removably snap fits on the main body open end to enclose the central compartment. A plurality of clip members are releasably engaged with respective pairs of the slot-like depressions at selective positions and receive and engage the free ends of resilient hold-down bands that extend across the patient's limb and/or limb extremities to resiliently maintain the limb or extremities in a position against the cassette holder relative to an X-ray cassette contained in the central compartment while obtaining intra-operative radiographs. The clips can also be engaged in slots in a support stand that supports the cassette holder in a vertical position.

15 Claims, 6 Drawing Sheets

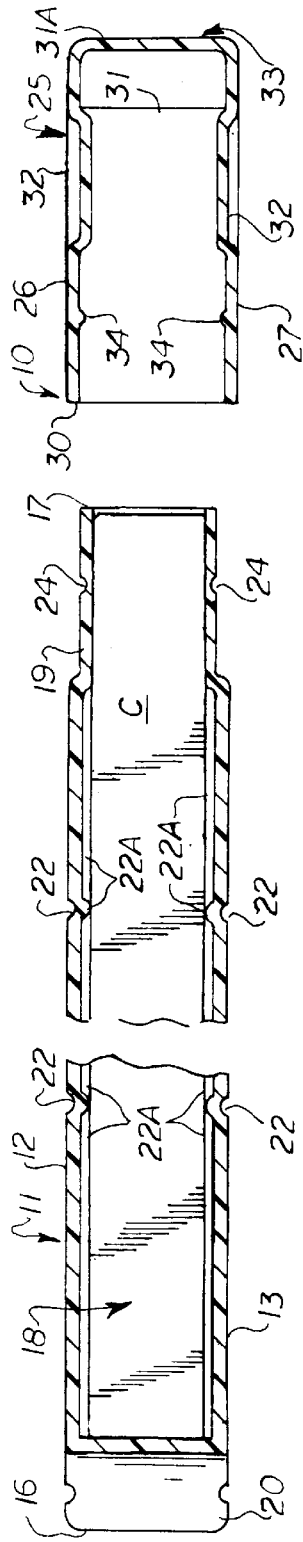
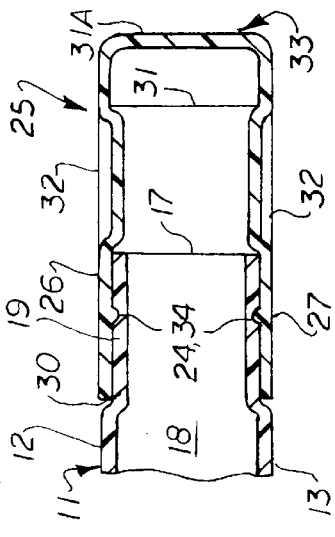
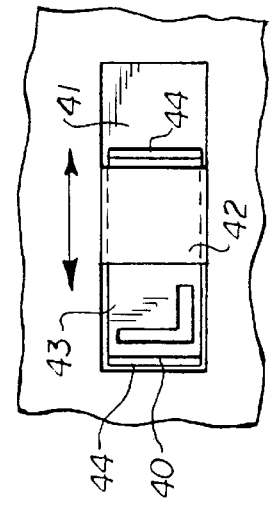
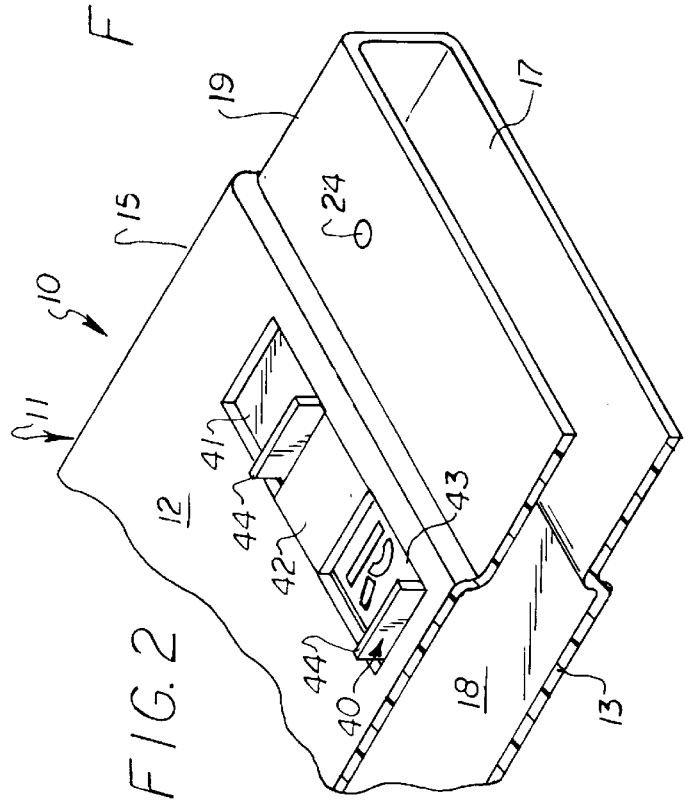

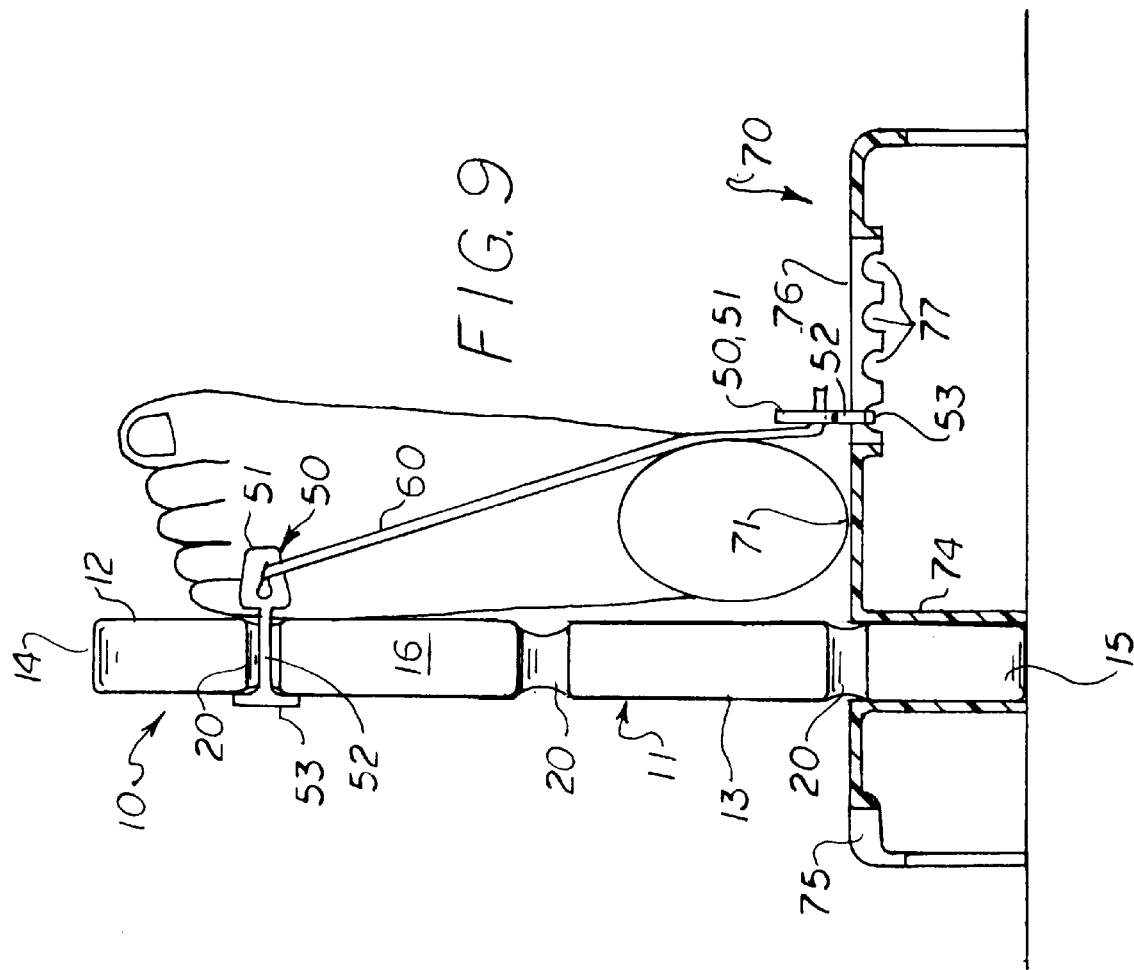

AUTOCLAVABLE X-RAY CASSETTE HOLDER WITH HOLD-DOWN MEANS

BACKGROUND OF THE INVENTION

1. Field of the Invention

This invention relates generally to X-ray cassette holders, and more particularly to a portable autoclavable X-ray cassette holder with hold-down means for positioning and holding the patient's limb from the hip or shoulder proximally and/or extremities in a position on the holder relative to the X-ray cassette contained therein which does not require an attendant to maintain proper position and completely eliminates radiation exposure to attendants.

2. Brief Description of the Prior Art

When taking X-rays of a patient's limb from the hip or shoulder proximally and/or remaining limb distally during surgical procedures (intraoperatively), it is common to place a sterile plastic bag over the X-ray cassette and position the limb and/or extremity on the X-ray cassette. In such situations the patient may be lying on an operating table and may not be conscious or may otherwise may be incapable of holding his or her limb in a particular position to be X-rayed. Thus, the patient's limb is usually held still by the physician or an attendant while the X-ray is being taken. However, very often the physician or attendant will move the limb or extremity or hold it improperly to avoid radiation exposure to himself or herself, resulting in a poor or inaccurate X-ray.

While holding the limb and/or extremity against the X-ray cassette, physicians and attendants are often exposed to radiation which, with repeated exposure over extended periods of time, is detrimental to their health.

There are several patents which disclose various X-ray cassette holders.

Griffiths, U.S. Pat. No. 4,961,502 discloses an X-ray cassette holder for use in an operating room which, in the preferred embodiment, is formed of a open ended rigid rectangular upper collar with a reduced rectangular receiver portion and a rectangular cover hinged at one side to the receiver portion and a flexible bag forms the bottom main body portion. In another embodiment, the holder is a hollow generally rectangular member with a reduced rectangular receiver portion at its open end and a rectangular cover hinged at one side to the receiver portion. The components are formed of rigid laminated cardboard or plastic which is capable of sterilization by irradiation. There is no suggestion of any means for holding or maintaining a patient's limb in a position relative to the X-ray cassette.

Malley, U.S. Pat. No. 5,327,912 discloses an X-ray poser having a sliding carriage to which a patient's forearm and hand may be strapped at a prescribed angle for evaluating carpal tunnel syndrome conditions. An X-ray cassette is removably received in a pair of L-shaped base members beneath the carriage.

Brotzman, U.S. Pat. No. 5,563,926 discloses a frame-like support for an X-ray cartridge which includes a flat base plate to be placed under the leg of a patient that has a series of slots and projections and an L-shaped X-ray cartridge support formed of U-shaped channels at one end of the base plate that support an X-ray cartridge. A patient's foot is supported against the X-ray cartridge and the patient's leg is strapped to the base plate by a tie-down strap formed of a length of gauze or surgical sponge.

Fick et al, U.S. Pat. No. 5,684,853 discloses a holder for a flexible X-ray cassette having a radiolucent top plate, a parallel bottom plate, rectangular side bars along three sides, and an upwardly resiliently biased interior pressure plate that urges the flexible cassette against the underside of the top plate. The cassette holder may be placed in a rigid rectangular support housing formed of a radiolucent top plate, a parallel bottom plate, and rectangular side bars along three sides with two of the side bars having resilient slides that urge the top plate of the cassette holder against the underside of the top plate of the housing. The housing is used to support heavy subjects above a cassette holder that is not itself sturdy enough to support the heavier subject. Both the cassette holder and the outer support housing are open at one end and there is no provision for holding or maintaining a patient's limb in a position relative to the X-ray cassette.

The present invention is distinguished over the prior art in general, and these patents in particular by an autoclavable X-ray cassette holder that removably receives and contains an X-ray cassette and maintains a patient's limb and/or extremities in a position on the holder relative to the X-ray cassette without requiring an attendant, thereby eliminating radiation exposure to the attendant. The holder has a thin rectangular hollow box-like main body formed of rigid radiolucent autoclavable material with an open end defining a central compartment surrounded by contiguous top and bottom walls, side walls, and an end wall. A plurality of slot-like depressions are formed along its side walls and end wall. An end cap removably snap fits on the main body open end to enclose the central compartment. A plurality of clip members are releasably engaged with respective pairs of the slot-like depressions at selective positions and receive and engage the free ends of resilient hold-down bands that extend across the patient's limb and/or limb extremities to resiliently maintain the limb or extremities in a position against the cassette holder relative to an X-ray cassette contained in the central compartment while obtaining intraoperative radiographs. The clips can also be engaged in slots in a support stand that supports the cassette holder in a vertical position.

SUMMARY OF THE INVENTION

It is therefore an object of the present invention to provide an autoclavable X-ray cassette holder which is portable easily transportable.

It is another object of this invention to provide a portable autoclavable X-ray cassette holder which removably receives and encloses X-ray cassettes of various sizes.

Another object of this invention is to provide a portable autoclavable X-ray cassette holder which allows accurate and reproducible radiographs of limbs to be taken without the need of an attendant or physician to maintain the proper position and thereby completely eliminates radiation exposure to attendants, physicians, and other operating room personnel.

Another object of this invention is to provide a portable autoclavable X-ray cassette holder having a plurality of resilient bands selectively positionable across a patient's limb or the limb extremities for holding the limb and/or extremities on the top surface of the holder relative to the X-ray cassette inside the holder.

A further object of this invention is to provide a portable X-ray cassette holder which is autoclavable and reusable.

A still further object of this invention is to provide a portable autoclavable X-ray cassette holder which is simple in construction, inexpensive to manufacture, and rugged and reliable in operation.

Other objects of the invention will become apparent from time to time throughout the specification and claims as hereinafter related.

The above noted objects and other objects of the invention are accomplished by an autoclavable X-ray cassette holder that removably receives and contains an X-ray cassette and maintains a patient's limb and/or extremities in a position on the holder relative to the X-ray cassette without requiring an attendant, thereby eliminating radiation exposure to the attendant. The holder has a thin rectangular hollow box-like main body formed of rigid radiolucent autoclavable material with an open end defining a central compartment surrounded by contiguous top and bottom walls, side walls, and an end wall. A plurality of slot-like depressions are formed along its side walls and end wall. An end cap removably snap fits on the main body open end to enclose the central compartment. A plurality of clip members are releasably engaged with respective pairs of the slot-like depressions at selective positions and receive and engage the free ends of resilient hold-down bands that extend across the patient's limb and/or limb extremities to resiliently maintain the limb or extremities in a position against the cassette holder relative to an X-ray cassette contained in the central compartment while obtaining intraoperative radiographs. The clips can also be engaged in slots in a support stand that supports the cassette holder in a vertical position.

BRIEF DESCRIPTION OF THE DRAWINGS

FIG. 2 is an isometric view of a corner portion of the X-ray cassette holder showing the reduced rectangular neck portion and the sliding left/right film identifier.

FIG. 3 is a longitudinal cross section of the X-ray cassette holder taken along line 3—3 of FIG. 1, showing and X-ray cassette in the interior compartment and prior to the end cap being installed.

FIG. 4 is a cross section of a portion of the X-ray cassette holder showing the end cap installed on the reduced rectangular neck portion.

FIG. 5 is a top plan view of a corner portion of the X-ray cassette holder showing the sliding left/right film identifier.

FIGS. 8 and 9 are front and side elevation views, respectively, showing a patient's foot secured by a number of bands to the portable autoclavable X-ray cassette holder supported vertically by the stand.

DESCRIPTION OF THE PREFERRED EMBODIMENT

Figure 1:
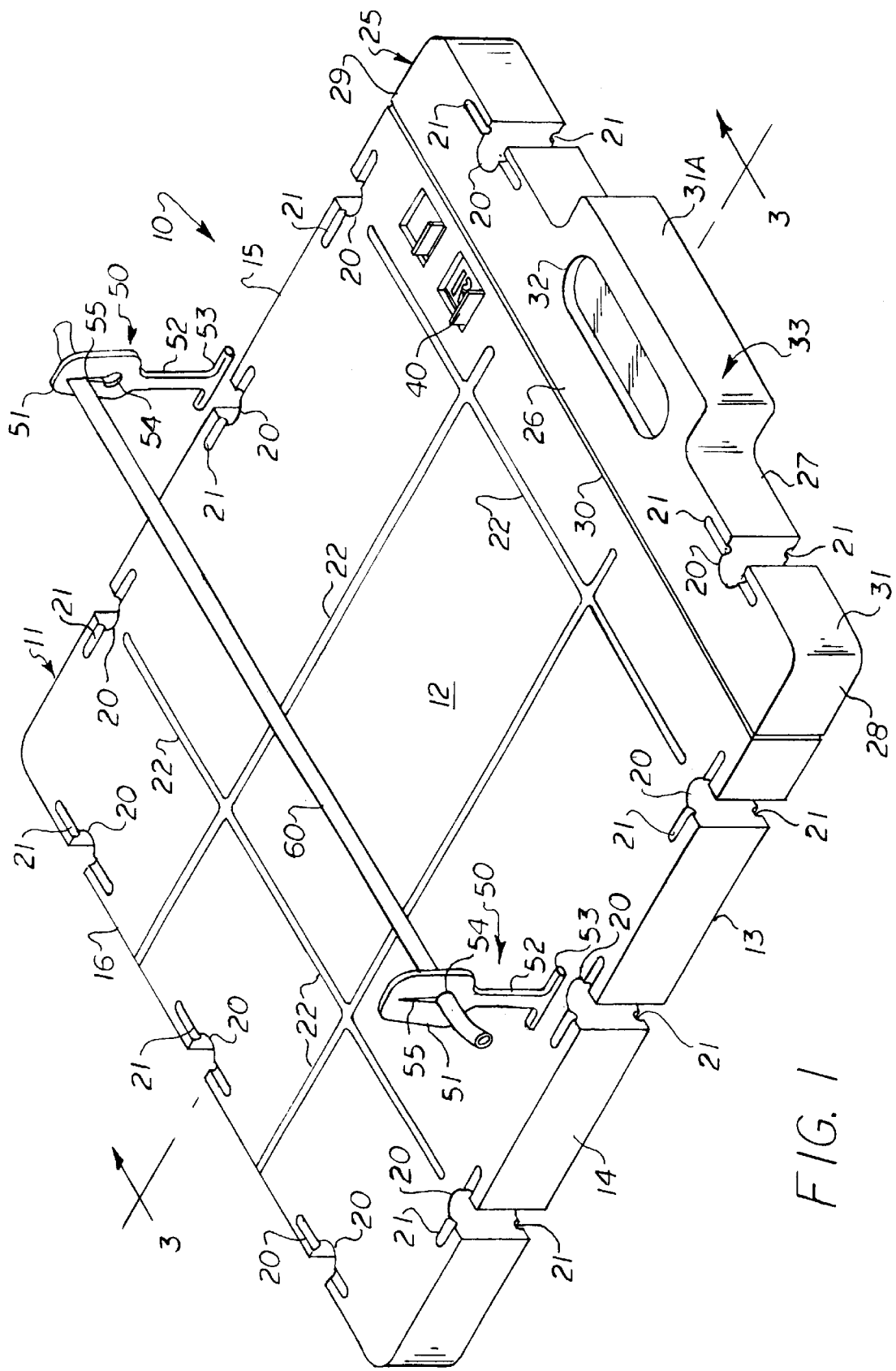
FIG. 1 is an isometric view of the portable autoclavable X-ray cassette holder in accordance with the present invention shown with a pair of clips and a resilient hold-down band in an unsecured position.

Referring to the drawings by numerals of reference, there is shown in FIGS. 1, 2, 3 and 4, a preferred portable autoclavable X-ray cassette holder 10 having a main body 11 and an end cap 20. The main body 11 and end cap 25 are molded of a lightweight thin-walled radiolucent plastic material which is capable of being sterilized by autoclaving (steam under pressure). The main body 11 and end cap 25 may be formed by injection molding, vacuum forming, or blow-molding upper and lower shells and bonding the two shells together along their sides by means conventional in the art.

The main body 11 is a hollow generally rectangular box-like member having opposed top and bottom walls 12 and 13, opposed side walls 14 and 15, an end wall 16, and an open end 17 defining a central compartment or cavity 18. As best seen in FIGS. 2 and 3, the open end 17 of the main body 11 has reduced rectangular neck portion 19 which is smaller in peripheral dimension than the main body portion.

Figure 6:
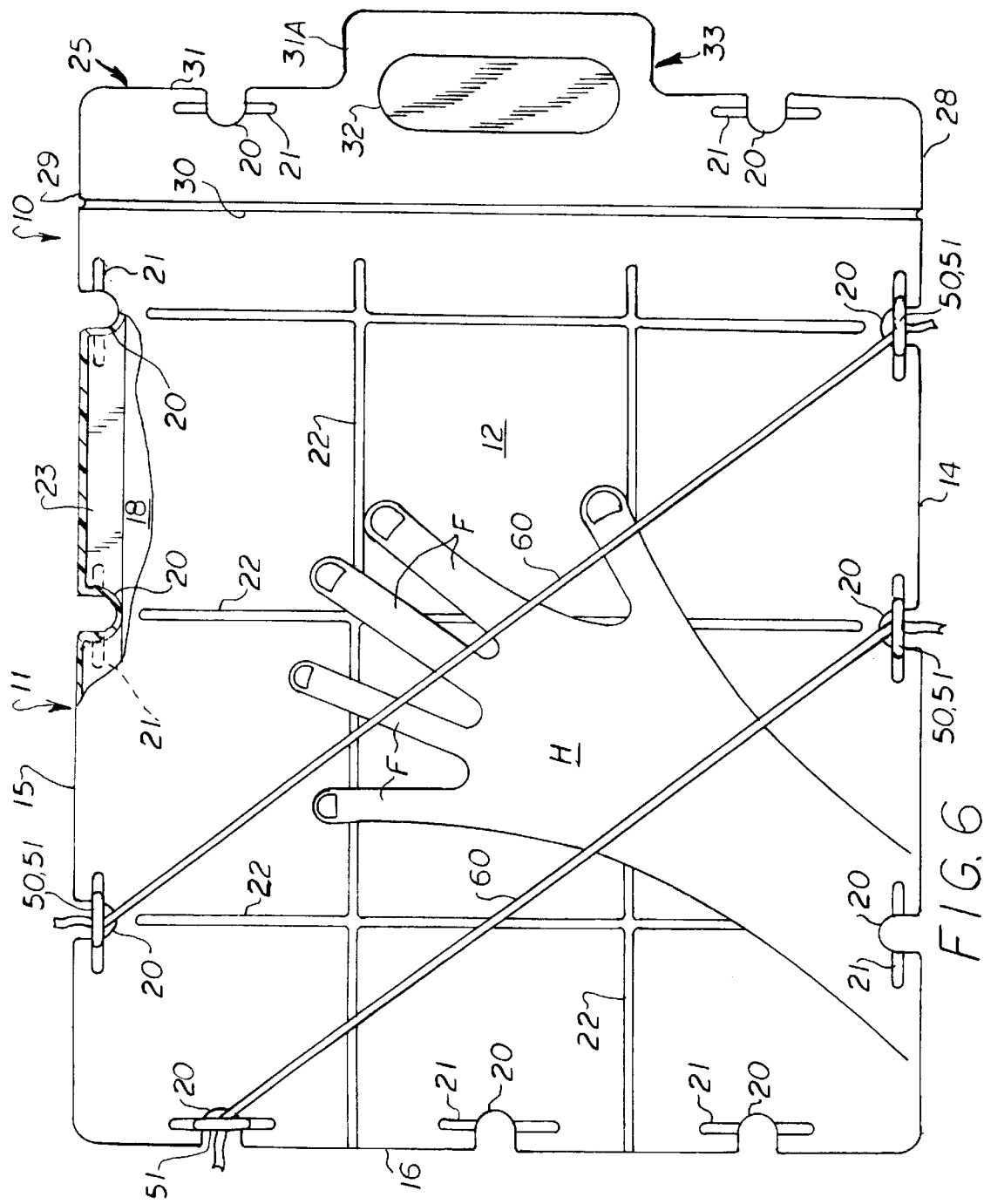
FIG. 6 is a top plan view showing the hand and fingers of a patient secured palm down on the top wall of the portable autoclavable X-ray cassette holder.

The opposed side walls 13 and 14 and end wall 15 of the main body 11 have a plurality of longitudinally spaced laterally inward extending slot-like depressions 20 formed therein. Short recessed grooves 21 formed in the top and bottom walls 12 and 13 extend laterally outward from opposed sides of each slot-like depression 20. A series of inwardly extending longitudinal and transverse grooves 22 are formed in the top and bottom walls of the 12 and 13 of the main body 11. The grooves 22 form short inwardly projecting longitudinal and transverse rails 22A in the interior of the main body for supporting an X-ray cassette C (FIG. 3), and also serve as structural stiffeners to strengthen the thin walled top and bottom surfaces and prevent deformation. As shown in FIG. 6, longitudinal side rails 23 formed on the interior of the main body 11 extend along the opposed sides 14 and 15 between the inwardly extending slot-like depressions 20 and are flush with the inner surfaces thereof to facilitate sliding the X-ray cassette C into the central cavity 18 and prevent its corners from abutting the depressions. As best seen in FIGS. 2 and 3, a plurality of adjacent spaced rounded depressions or dimples 24 are formed in the exterior top and bottom surfaces of the rectangular neck portion 19 of the main body 11.

The end cap 25 is a hollow generally rectangular member having opposed top and bottom walls 26 and 27, opposed side walls 28 and 29, an open end 30, and an end wall 31. The end wall 31 has a central outwardly extending portion 31A which has a rectangular depression 32 formed in its top and bottom surfaces that define a hand grip 33 on the end cap 25. The end wall 31 of the end cap 25 has a plurality of longitudinally spaced laterally inward extending slot-like depressions 20 and laterally extending short grooves 21 in the top and bottom walls 26 and 27, as previously described, formed therein.

As shown in FIGS. 3 and 4, a plurality of adjacent spaced inwardly facing rounded protuberences 34 are formed on the interior top and bottom surfaces of the end cap 25 in alignment with the dimples 24 in the neck portion 19 of the main body 11. The interior of the end cap 25 is sized to be slidably received on the rectangular neck portion 19 of the main body 11 and its protuberences 34 are sized to snap fit into the dimples 24 on the neck portion 19 to firmly retain the end cap on the neck portion to prevent accidental removal, but to allow the end cap to be manually pulled off of the neck portion upon application of sufficient pulling force.

The exterior surface of the main body 11 and end cap 25 may be smooth or may be provided with a rough surface texture to facilitate manual gripping and manipulation and to reduce the likelihood of accidental slippage of a limb or extremities placed on its top wall 12. The top wall 12 may also be provided with various markings, guide lines, or indicia to facilitate proper positioning of the limb or extremities.

FIGS. 2 and 5 show a corner of the cassette holder 10 having a sliding tab left/right film identifier 40. The top wall 12 is provided with a flat rectangular depression 41 with a web 42 formed of non-radiolucent material extending thereabove to define left and right sides. As seen in FIG. 5, a flat rectangular tab 43 with upwardly extending ends 44 formed of non-radiolucent material is slidably received beneath the web 42 in the depression 41 and has the letters "L" and "R" punched out of its flat portion in laterally spaced relation. The tab 43 is sized such that only one letter is covered by the web 42 leaving the other letter exposed. The user can place a finger on one of the upstanding ends 44 of the tab 43 and manually slide the tab to the left or right to expose the appropriate one of the letters. When the radiograph is taken, the letter which is uncovered will show as a white letter on the film.

Referring again to FIG. 1, a plurality of clips 50 and elastic hold-down bands 60 are provided with the X-ray cassette holder 10. The clips 50 can be removably secured in the slot-like depressions 20 along the opposed side walls 14 and 15 and the end wall 16 of the main body 11 or the end cap 25. The clips 50 are preferably formed of a semi-rigid plastic material and have a generally rectangular upper portion 51 and an inverted T-shaped lower portion defined by a thin narrow shank portion 52 extending downwardly from the upper portion and terminating in a horizontal rod-like bar 53 at the bottom end. The length of the shank portion 52 is slightly greater than the height of the slot-like depressions 20 and the rod-like bar 53 is sized to be received in selected ones of the short grooves 21 on the underside of the main body 11 or end cap 25.

The generally rectangular upper portion 51 of each clip 50 has a central inverted generally keyhole-shaped aperture defined by a circular bottom portion 54 and a narrow inverted V-shaped vertical slot 55 extending upwardly therefrom with upwardly and inwardly converging sides.

The hold-down bands 60 are elongate resilient members, such as a length of surgical tubing which is larger in cross section than width of the inverted V-shaped slot 55 of the keyhole shaped aperture. The hold-down bands 60 may be disposable. The free end of an elastic band 60 is inserted through the circular bottom portion 55 of the aperture 54 in a respective clip 50 and then pulled upwardly into the narrow inverted V-shaped slot 55 to become wedged therein. The length, and thus the tension or tightness, of the band 60 can be adjusted to the particular hold-down requirements by pulling one end of the band down into the circular portion 54 and stretching or loosening the band and then pulling it up to wedge it back into the V-shaped slot 55. As explained hereinafter, the hold-down bands 60 are stretched across a patients limb or extremities to resiliently bias the limb or extremities against the top wall 12 of the cassette holder.

The clips 50 are removably installed on the main body 11 by securing a clip at one or both ends of a hold-down band 60, as described above, and then placing the shank portion 52 of the clip into slot-like depression 20 with its horizontal bar 53 received on the underside of the main body 11 in the short grooves 21 extending laterally outward from the slot-like depression 20 and its rectangular upper portion 51 extending above and transverse to the slot-like depression. When tension is applied to the hold down-band 60 the horizontal bar 53 at the bottom of the clip 50 is resiliently pulled into engagement with the short grooves 21. Pairs of the clips 50 may be installed in selected pairs of the slot-like depressions 20 on opposed side walls 14 and 15 or a side wall and the end wall 16 of the main body 11 or end cap 25.

Figure 7:
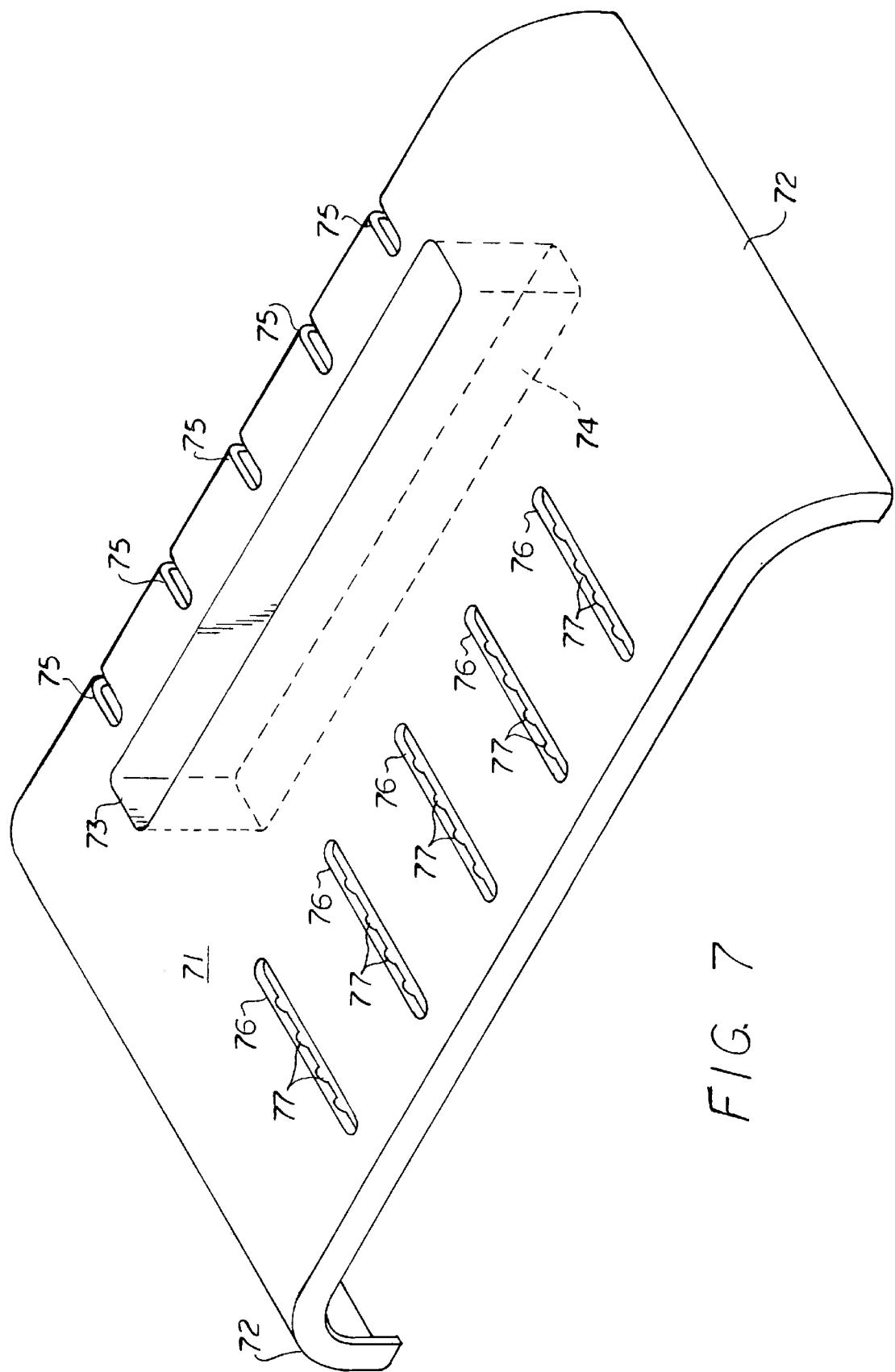
FIG. 7 is an isometric view of a stand for supporting the portable autoclavable X-ray cassette holder in a vertical position.

FIG. 7 shows a stand 70 for supporting the portable autoclavable X-ray cassette holder 10 in a vertical position. The stand 70 has a flat rectangular top wall 71 which curves downwardly at two opposed ends to form legs 72 to support the top wall a distance above a supporting surface.

Figure 8:
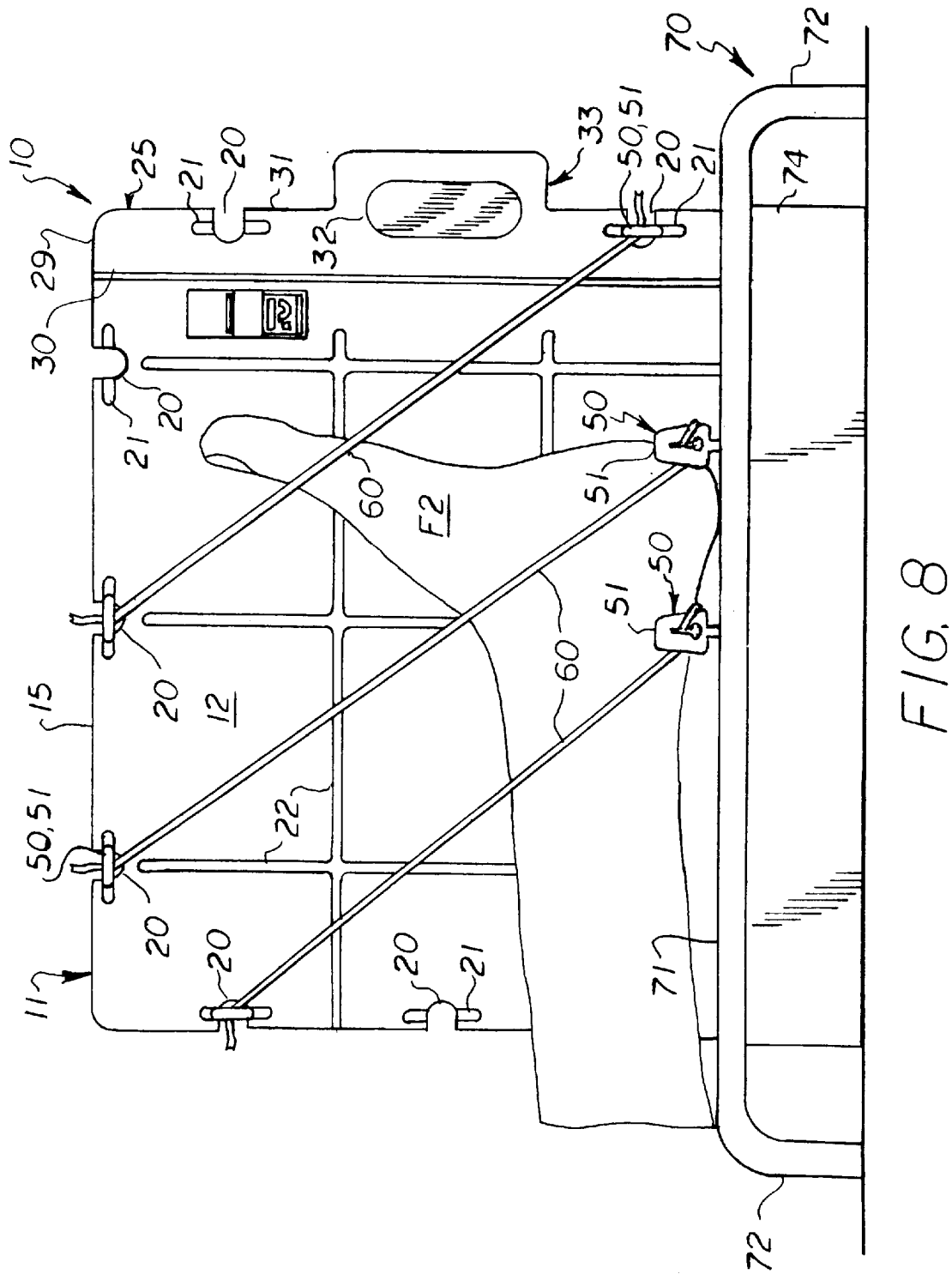

The top wall 71 has a rectangular opening 73 near one side edge surrounded by a rectangular wall 74 extending downwardly from the top wall. The opening 73 is slightly wider and longer than the main body 11 of the cassette holder 10 with the end cap 25 installed thereon to allow the cassette holder to be slidably installed in the opening and supported by the stand in a vertical position with the end cap facing upward or to one side, as shown in FIGS. 8 and 9.

The top wall 71 of the stand 70 has a plurality of adjacent longitudinally spaced short slots 75 extending inwardly a distance along the side edge closest to the rectangular opening 73 and a plurality of parallel spaced elongate slots 76 disposed a distance outwardly from the rectangular opening 73. The elongate slots 76 are surrounded by a depending lip having a series of parallel spaced concave notches 77 formed in its bottom surface in laterally spaced relation.

The clips 50 can be removably installed on the stand 70 by securing a clip at one or both ends of a hold-down band 60, as described above, and then placing the shank portion 52 of the clip in a short slot 75 with its horizontal bar 53 received beneath the slot and its rectangular upper portion 51 extending above and transverse to the slot. The clips 50 can be removably installed in the elongate slots 76 in the stand 70 by securing a clip at one or both ends of a hold-down band 60, lowering the inverted T-shaped lower portion and horizintal bar 53 of the clip through the slot parallel to the axis of the slot, and then turning the clip 90° to the slot axis such that the horizontal bar 53 of the clip is received in the appropriate laterally spaced pair of concave notches 77 on the underside of the slot.

OPERATION

The portable autoclavable X-ray cassette holder 10 is particularly suited for use in taking X-rays in a sterile environment such as an operating room during surgical procedures while a patient is on an operating table. In such situations, the patient may be incapable of holding his or her limb in a particular position to be X-rayed. Prior to use, the X-ray cassette holder is sterilized by autoclaving and receives a non-sterile X-ray cassette. Typically, the non-sterile X-ray cassette is inserted by a non-sterile technician into the sterilized X-ray cassette holder which is held by a sterile member of the operating team.

To use the portable autoclavable X-ray cassette holder 10, the end cap 25 is removed, and a conventional non-sterilized X-ray cassete C of the appropriate size is slid into the interior of the main body and supported on the rails 22A (FIG. 3), and the end cap 25 is pushed onto the neck portion 19 and snap fitted thereon to secure the X-ray cassette within the holder 10.

The limb or extremity of the patient is placed on the top wall 12 with the portion to be X-rayed or radiographed over the X-ray cassette C. The free ends of one or more elastic bands 60 are inserted through the circular bottom portion 54 of the keyhole-shaped aperture in a respective clip 50 and then pulled upwardly into the narrow inverted V-shaped slot 55 to become wedged therein. The clips 50 at each end of the bands 60 are then secured in selected pairs of the slot-like depressions 20 on opposed side walls 14 and 15 or on a side wall and the end wall 16 of the main body 11 or the end cap 25, as required.

The length, and thus the tension or tightness, of the band 60 can be adjusted to the particular hold-down requirements by pulling one end of the band 60 down into the circular portion 54 of the clip 50 and stretching or loosening the band and then pulling it up to wedge it back into the V-shaped slot 55 and thereby resiliently bias the limb or extremities against the top wall 12 of the cassette holder while the X-ray or radiograph is taken.

It should be noted that once the cassette holder and limb or extremity are properly positioned and secured, it is not necessary for an attendant or physician to hold the limb or extremity while the X-ray or radiograph is taken. Thus, the present cassette holder completely eliminates radiation exposure to the attendant or physician. FIGS. 6, 8, and 9 illustrate typical examples of how limbs and extremities may be positioned.

FIG. 6 shows the hand H of a patient secured palm down on the top wall 12 of the cassette holder 10 with the fingers F spread apart and secured over the X-ray cassette which is in the holder 10 by a plurality of resilient hold-down bands 60.

FIGS. 8 and 9 are front and side elevation views, respectively, showing the X-ray cassette holder 10 supported vertically in the stand 70 and a patient's foot F2 secured by a number of bands 60 to the top wall 12 of the X-ray cassette holder by a plurality of resilient hold-down bands 60 extending between the stand and the X-ray cassette holder.

While this invention has been described fully and completely with special emphasis upon a preferred embodiment, it should be understood that within the scope of the appended claims the invention may be practiced otherwise than as specifically described herein.

What is claimed is:

1. A portable X-ray cassette holder for containing an X-ray cassette with hold-down means for maintaining a patient's limb and/or the limb extremities in a position on the holder relative to the X-ray cassette without requiring an attendant, said holder comprising:

a hollow generally rectangular box-like main body formed of rigid radiolucent autoclavable material having an open end and a central compartment surrounded by contiguous opposed top and bottom walls, opposed side walls, and an end wall;

a plurality of longitudinally spaced laterally inward extending slot-like depressions formed along said main body opposed side walls and end wall;

said main body sized to receive a patient's limb from the hip or shoulder proximally and/or the limb extremities, and said central compartment sized to contain an X-ray cassette;

a generally rectangular end cap removably received on said main body open end to enclose said central compartment;

a plurality of clips each sized and shaped to be releasably engaged with a respective said slot-like depression and having band receiving means for releasably receiving and engaging a free end of a resilient band; and a plurality of resilient bands capable of extending across said patient's limb and/or limb extremities and having opposed free ends capable of being releasably engaged with respective pairs of said clips at selective positions to resiliently maintain said limb and/or limb extremities on said main body top wall relative to an X-ray cassette contained in said central compartment during radiation without requiring an attendant, thereby eliminating radiation exposure to the attendant.

2. The portable X-ray cassette holder according to claim 1, further comprising
   hand grip means on said end cap.

3. The portable X-ray cassette holder according to claim 1, further comprising
   a series of inwardly facing longitudinal and transverse rails in said main body central compartment for supporting an X-ray cassette therein.

4. The portable X-ray cassette holder according to claim 1 wherein
   said main body open end is surrounded by a reduced rectangular neck portion with contiguous opposed top and bottom walls and opposed side walls;
   said end cap is a hollow generally rectangular configuration having opposed top and bottom wall, opposed side walls, an end wall, and an open end; and
   said end cap open end is slidably received on said reduced rectangular neck portion.

5. The portable X-ray cassette holder according to claim 4 further comprising
   a plurality of longitudinally spaced inward extending slot-like depressions formed along said end cap end wall; and
   said clips are selectively engageable with selected said slot-like depressions in said end cap end wall and with said slot-like depressions along said main body opposed side walls and end wall and said resilient bands opposed free ends are capable of being releasably engaged with respective pairs of said clips to releasably maintain said patient's limb and/or limb extremities in a position on said main body top wall.

6. The portable X-ray cassette holder according to claim 4 further comprising:
   a plurality of adjacent spaced concave dimples in exterior surfaces of said rectangular neck portion top and bottom walls; and
   a plurality of adjacent spaced inward facing rounded protuberences on the interior of said end cap top and bottom surfaces sized and spaced to snap fit into said concave dimples on said rectangular neck portion when said end cap is slidably received thereon to prevent accidental removal and allow said end cap to be manually pulled off of said rectangular neck portion upon application of sufficient force.

7. The portable X-ray cassette holder according to claim 1 further comprising
   a support stand having a generally rectangular top wall disposed a distance above a support surface with an aperture therethrough configured to removably receive and support said cassette holder in a vertical position.

8. The portable X-ray cassette holder according to claim 7 further comprising
   a plurality of adjacent longitudinally spaced slots in said support stand top wall; and
   said clips are selectively engageable with selected slots in said support stand top wall and with said slot-like depressions along said main body opposed side walls and end wall and said resilient bands opposed free ends are capable of being releasably engaged with respective pairs of said clips to releasably maintain said patient's limb and/or limb extremities in a position on said support stand top wall and said main body top wall relative to an X-ray cassette contained in said central compartment during radiation without requiring an attendant, thereby eliminating radiation exposure to the attendant.

9. The portable X-ray cassette holder according to claim 7 further comprising a plurality of adjacent longitudinally spaced short slots along a side edge of said support stand top wall; and said clips are selectively engageable with selected short slots in said support stand top wall and with said slot-like depressions along said main body opposed side walls and end wall and said resilient bands opposed free ends are capable of being releasably engaged with respective pairs of said clips to releasably maintain said patient's limb and/or limb extremities in a position on said support stand top wall and said main body top wall relative to an X-ray cassette contained in said central compartment during radiation without requiring an attendant, thereby eliminating radiation exposure to the attendant.

10. The portable X-ray cassette holder according to claim 1 wherein each said clip has a generally rectangular upper portion and an inverted T-shaped lower portion;

said T-shaped lower portion sized and shaped to be releasably engaged with a respective said slot-like depression with said generally rectangular upper portion extending above said respective slot-like depression;

said generally rectangular upper portion having a central aperture; and each said resilient band having a length and said opposed ends of each band being capable of being releasably engaged in said central aperture of a said clip at selective positions along its length to adjust the tension at which said limb and/or limb extremities is resiliently maintained on said main body top wall.

11. The portable X-ray cassette holder according to claim 1 further comprising manually movable film identifier means on said main body top wall including indicia that is reproduced as an image on X-ray film contained in said X-ray cassette during radiation.

12. The portable X-ray cassette holder according to claim 1 wherein said plurality of resilient bands are formed of lengths of surgical tubing.

13. The combination of a portable X-ray cassette holder for containing an X-ray cassette and a plurality of hold-down elements for maintaining a patient's limb and/or the limb extremities in a position on the holder relative to the X-ray cassette without requiring an attendant;

said holder comprising a hollow generally rectangular box-like main body formed of rigid radiolucent autoclavable material sized to receive a patient's limb from the hip or shoulder proximally and/or the limb extremities, an open end, and a central compartment surrounded by contiguous top and bottom walls, opposed side walls and an end wall, and a plurality of longitudinally spaced laterally inward extending slot-like depressions formed along said side walls and end wall, said central compartment sized to contain an X-ray cassette;

a generally rectangular end cap removably received on said main body open end to enclose said central compartment; and said plurality of hold-down elements each comprising an elongate resilient band capable of extending across said patient's limb and/or limb extremities, and a clip element releasably engaged on opposed ends of each band;

each of said clip elements sized and shaped to be releasably engaged with a respective said slot like depression with said resilient band extending across said patient's limb and/or limb extremities to releasably maintain said patient's limb and/or limb extremities in a position on said main body top wall relative to an X-ray cassette contained in said central compartment during radiation without requiring an attendant, thereby eliminating radiation exposure to the attendant.

14. The combination according to claim 13 wherein said plurality of resilient bands are formed of lengths of surgical tubing.

15. The combination according to claim 13 wherein each said clip has a generally rectangular upper portion and an inverted T-shaped lower portion;

said T-shaped lower portion sized and shaped to be releasably engaged with a respective said slot-like depression with said generally rectangular upper portion extending above said respective slot-like depression;

said generally rectangular upper portion having a central aperture; and each said resilient band having a length and said opposed ends of each band being capable of being releasably engaged in said central aperture of a said clip at selective positions along its length to adjust the tension at which said limb and/or limb extremities is resiliently maintained on said main body top wall.

* * * * *